United States Patent [19]

Lhoste et al.

[11] Patent Number: 4,621,768

[45] Date of Patent: Nov. 11, 1986

[54] DEVICE FOR DIFFUSING VOLATILE LIQUIDS

[75] Inventors: Jean-François Lhoste, Chartres; Thierry Delage, Paris, both of France

[73] Assignee: Reckitt & Colman S.A., France

[21] Appl. No.: 784,758

[22] Filed: Oct. 7, 1985

[30] Foreign Application Priority Data

Oct. 9, 1984 [FR] France ................. 84 15473

[51] Int. Cl.⁴ .................................. A61L 9/12
[52] U.S. Cl. ..................... 239/44; 239/51.5; 239/59
[58] Field of Search ............. 239/44, 47, 48, 49, 239/50, 51.5, 57–59, 34, 145; 222/507

[56] References Cited

FOREIGN PATENT DOCUMENTS 0028852 5/1981 European Pat. Off. ............... 239/44
715344 11/1941 Fed. Rep. of Germany ........ 239/44
1293604 11/1972 United Kingdom ............... 239/47

Primary Examiner—Joseph F. Peters, Jr.
Assistant Examiner—Mary Beth O. Jones
Attorney, Agent, or Firm—Browdy and Neimark

[57] ABSTRACT

This invention relates to a diffusing device for volatile liquids to affect the immediate environment, or perfume or deodorize a room; such device comprising a bottle (1) containing the liquid for diffusion (2), in which a wick (M) is partially immersed; a cover cap (3) fitted to the said bottle by means of a snap-on system (3a), capable of being rotated but not moved in a vertical direction, and provided with slits or ports (F) for the passage of the air; a wick-holder (11-13) fitted to the neck (6) of the said bottle by means of a snap-on system and prevented from rotating, and taking the form of a sleeve provided with slits or ports (V) for the passage of air and with an external screw thread; and an internal cap (10) consisting of an internally-threaded skirt (15) designed to engage with external thread (16) of the said wick holder, and having in addition vertical grooves on the outside (14) designed slidably to engage with a vertical sleeve (9) which forms an integral part of the upper portion of the aforesaid cap (3), and of an internal sleeve (12) forming a sealing-cap for aforesaid wick.

1 Claim, 7 Drawing Figures

DEVICE FOR DIFFUSING VOLATILE LIQUIDS

This invention relates to a device for diffusing volatile liquids in order to affect the immediate environment, as for instance the atmosphere of a room, by perfuming or deodorising it.

There are already numerous devices designed for this purpose. Nearly all of them consist of a wick impregnated with the volatile liquid that it is desired to vapourise into the room, together with some means of bringing the said wick into contact with the surrounding air, when the device is in use, and of protecting it from such contact, when it is not.

Generally the wick is partially immersed in a liquid contained in a bottle, and it is necessary to bring that part of the wick which is not in the liquid into contact with the air. This is done by pulling the wick out of the bottle after removing a cap from the latter, or by unscrewing the cap to a greater or lesser degree in order to bring the desired amount of a protective sleeve clear of the wick and so allow air to circulate between the sleeve and the bottle-cap, which is provided with holes or slits for the purpose; or else by removing a protective sleeve from the wick and then bringing the latter directly into contact with some other absorbent material held in the bottle-cap, which is provided with slits or holes to permit the circulation of air.

The principles on which these various devices work are illustrated in greatly simplified form in FIGS. 1 to 3, attached.

Thus FIG. 1 shows a bottle (1) containing a volatile liquid (2), in which a wick (M) is partially immersed. This bottle is fitted with a cap or stopper (3). To allow the liquid (2) to vaporise into the atmosphere, all that is needed is to unscrew and remove the cap (3) and pull a greater or lesser length of the wick (M) out of the bottle by means of a ring (4). To stop the diffusion of the liquid, the process is reversed. Apart from the necessity of carrying out all these operations, it is clear that the device is unsightly when in use and that care must be taken not to lose the cap (3); otherwise one wastes liquid when diffusion is not required, as there is no means of stopping it, and the device cannot be carried from place to place without risk of spillage.

Similarly, FIG. 2 shows a bottle (1) with its liquid, in which the wick (M) is partially immersed. The upper part of the wick is protected by a sleeve (5), which is an integral part of the inside of the cap or closure (3). The vertical skirt of this cap screws on to the outside surface of the bottle (1). The upper part of the skirt is provided at (F) with slits or ports. The neck (6) of the bottle is held in contact with the sleeve (5) by a screw thread. To permit diffusion, one simply unscrews the cap (3). The air then circulates through the space freed by the withdrawal of the sleeve from the neck (6) and through the slits or ports (F) in the cap (3), taking with it vapour from the liquid impregnating the portion of the wick (M) that is thus exposed to the air. There is still an aesthetic problem, in that unscrewing the cap (3) increases the height of the device, thus altering its overall shape.

Finally, FIG. 3 illustrates a bottle (1) with its volatile liquid (2), in which the wick (M) is partially immersed. The cap or closure (3) is held on to the bottle (1), e.g. by a snap-on system or a screw thread at (7). That part of the wick (M) which projects from the neck (6) of the bottle (1) is protected by an inner cap (5) that screws on to the neck. In addition, inside the cap (3) there is a disc (8) of some suitable absorbent material such, for example, as cellulose foam or something similar. This disc is fitted in such a way that, when the inner cap (5) is removed, it comes into contact with the upper part of the wick (M). Thus, when one wants to use the device, one first removes the outer cap (3), then unscrews and removes the inner cap (5), after which one replaces the outer cap, tightening it until the wick (M) meets the disc (8). To stop diffusion, the procedure is reversed. It is clearly necessary to make sure not to lose the inner cap (5), in order to avoid wasting any of the diffusion product. Naturally, the skirt of the outer cap (3) is provided at (F) with slits or ports to allow air to circulate, so, in the event of the inner cap (5) being lost, there is of course no means of entirely stopping diffusion of the liquid, or of carrying the device from place to place without risk of spillage.

The invention presented here eliminates the disadvantages that we have indicated above, both from the aesthetic and from the practical point of view. It involves a wick-type diffuser which can be made liquid-tight in order to avoid any unwanted diffusion of the product when it is in the "closed" position, and which allows the degree of diffusion of the volatile liquid to be regulated by varying the through-put air and the diffusion-surface exposed to the airflow, without altering the original shape of the device itself.

The diffusor in question consists essentially of a bottle containing the liquid for diffusion, with a partially immersed wick; of a cap or closure that snaps on to the bottle and can be rotated on its axis without being moved vertically, and that is provided with slits or ports to permit the passage of air; of a wick-holder that snaps on to the neck of the bottle but is prevented from rotating, in the shape of a sleeve with air-slits or ports and an external screw-thread; and an internal cap comprising an internally-threaded skirt that engages with the external thread of the wick-holder mentioned above, as well as external vertical grooves designed to engage with a vertical sleeve forming an integral part of the upper part of the cap, and also an internal sleeve that makes a liquid-tight cap for the wick itself.

Other characteristics of the invention, and its advantages, will emerge more clearly from the description below, relating to the attached FIGS. 4 to 7, in which.

Figure 1:
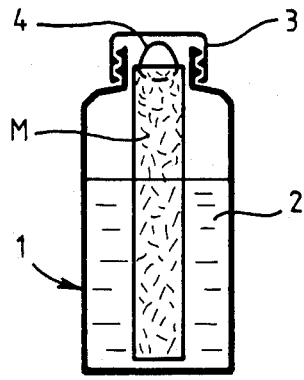
Figure 2:
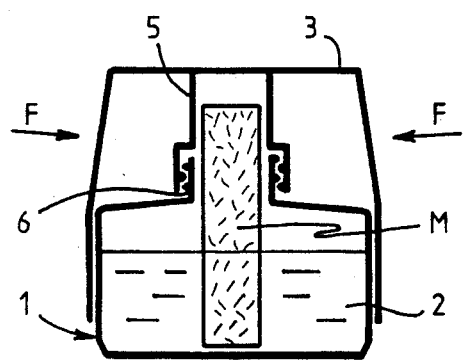
Figure 3:
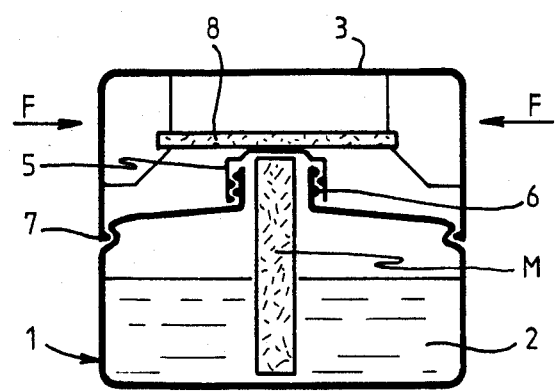

With reference to these figures, the diffusor that is the subject of the invention comprises a bottle (1) containing the volatile liquid (2), in which the wick (M) is partially immersed. The projecting part of this wick is protected, as will be seen below, by a means that will be described later. The upper part of the bottle (1) is made up of a cap or closure (3), of a suitable shape, which snaps on to the bottle (1) at 3a, and is provided all round with what we will call aeration slits or ports, (F). The upper part of this cap has inside it a sleeve (9), which is provided with vertical grooves designed to engage with the outside of an internal sleeve (10), which has an internal thread (15) that itself engages with the external thread (16) of a wick-holder (11) provided all round with slits or ports (V). An internal skirt, (12) fitted to the sleeve (10) forms a cap over the projecting upper part of the wick (M). The wick is in turn supported and held in a vertical position by a cylindrical component (13) with flared edges, which snaps on to the neck (6) of the bottle (1) and at the same time forms an integral part of the wick-holder (11).

Figure 4:
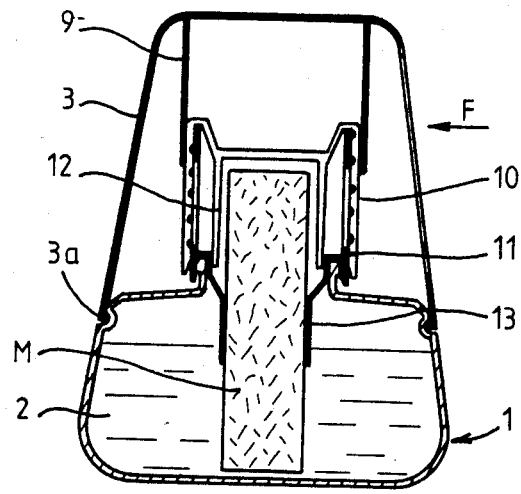
FIG. 4 is a sectional elevation diagram of a diffusor constructed according to the invention, in the "off" position.
Figure 5:
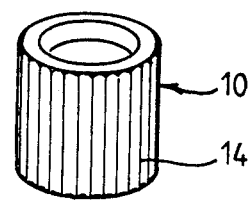
FIG. 5 is a perspective drawing of a single detail from FIG. 4.
Figure 7:
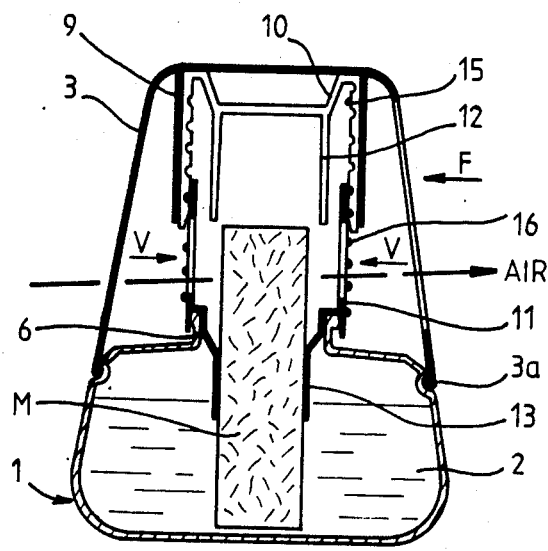
FIG. 7 is a corresponding diagram to FIG. 4, illustrating the "on" position.
Figure 6:
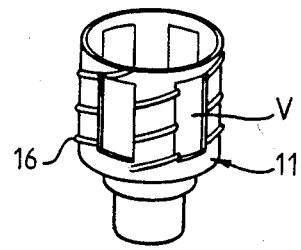
FIG. 6 is a perspective drawing of another single detail from FIG. 4.

When the diffusor is not in use, the internal sleeve (10) is in its lowest position, as shown in FIG. 4. It blocks the slits (V) in the wick-holder (11) and its skirt (12) forms a cap on the upper portion of the wick (M). As no air can enter, the liquid (2) cannot escape into the atmosphere. There is a perfect seal. When it is desired to diffuse the vapour from the volatile liquid, all that is necessary is to twist the cap (3). This rotatory movement provides a force which is transmitted through the sleeve (9) and the grooves (14) on the outside of the internal sleeve (10) to rotate this last, which then moves upwards. This unblocks the slits or ports (V) in the wick-holder (11) and allows air to circulate both through the slits or ports (F) in the cap and through the slits or ports (V) in the wick-holder. This means that the opening of these slits or ports can be regulated in accordance with the amount by which the internal sleeve (10) is raised, this being dependent on the number of turns given to the cap (3).

As twisting this cap makes no difference to the general appearance of the device, the latter's aesthetic characteristics are maintained, the amount of air circulating inside the device being regulated without altering the relative positions of the bottle and its cap.

The device that is the subject of the invention can be turned off at any moment, stopping diffusion entirely and at the same time providing a liquid-tight unit that can be carried about without problems; there is no need to take it apart or to replace a cap.

As in any diffusor, the volatile liquid can of course be a perfume, an antiseptic, an air-purifier, etc.

Similarly the wick (M) can be made of any material that will provide capilary diffusion, such as fibre, paper, cellulose, felt, cellulose acetate, polyester, polypropylene etc.

Needless to say, this invention has been described purely for purposes of explanation and to no restrictive effect, so that any modifications not altering its principles can be introduced, without going outside its limits.

We claim:

1. A diffusing device for volatile liquids to affect the immediate environment, or perfume or deodorise a room; such device comprising a bottle (1) containing the liquid for diffusion (2), in which a wick (M) is partially immersed; a cover cap (3) fitted to the said bottle by means of a snap-on system (3a), capable of being rotated but not moved in a vertical direction, and provided with slits or ports (F) for the passage of air; a wick-holder (11-13) fitted to the neck (6) of the said bottle by means of a snap-on system and prevented from rotating, and taking the form of a sleeve provided with slits or ports (V) for the passage of air and with an external screw thread; and an internal cap (10) consisting of an internally-threaded skirt (15) designed to engage with said external thread (16) of the said wick-holder, and having in addition vertical grooves on the outside (14) designed slidably to engage with a vertical sleeve (9) which forms an integral part of the upper portion of the aforesaid cap (3), said internal cap further consisting of an internal sleeve (12) forming a sealing-cap for aforesaid wick.

* * * * *